United States Patent [19]

Beck

[11] 4,054,441

[45] Oct. 18, 1977

[54] SUBSTITUTED (α,α,α-TRIFLUORO-2,6-DINITRO-P-TOLYL)-HYDRAZINES

[75] Inventor: James Richard Beck, Indianapolis, Ind.

[73] Assignee: Eli Lilly and Company, Indianapolis, Ind.

[21] Appl. No.: 618,999

[22] Filed: Oct. 2, 1975

[51] Int. Cl.² ............... C07D 211/98; C07D 207/50; A01N 9/22
[52] U.S. Cl. ............................ 71/94; 71/95; 260/293.79; 260/326.85
[58] Field of Search ............. 260/293.79, 326.85; 71/94, 95

[56] References Cited

U.S. PATENT DOCUMENTS

| | | | |
|---|---|---|---|
| 3,466,329 | 9/1969 | Soper | 260/326.85 |
| 3,617,252 | 11/1971 | Hunter et al. | 260/326.85 |
| 3,686,230 | 8/1972 | Maravetz | 260/293.79 |
| 3,867,452 | 2/1975 | Wilcox | 260/293.77 |
| 3,891,706 | 6/1975 | Wilcox | 260/293.79 |

*Primary Examiner*—Norma S. Milestone
*Attorney, Agent, or Firm*—Dwight E. Morrison; Everet F. Smith

[57] ABSTRACT

Novel substituted (α,α,α-trifluoro-2,6-dinitro-p-tolyl)-hydrazines, active as herbicides, together with herbicidal methods and compositions employing said novel compounds.

7 Claims, No Drawings

SUBSTITUTED (α,α,α-TRIFLUORO-2,6-DINITRO-P-TOLYL)HYDRAZINES

BACKGROUND OF THE INVENTION

1. Field of the Invention

This invention relates to substituted (α, α, α-trifluoro-2,6-dinitro-p-tolyl)hydrazines active as herbicides.

2. Description of the Prior Art

In the prior art, Wilcox, U.S. Pat. No. 3,867,452 Feb. 18, 1975), described herbicidal 2-nitrophenylhydrazines, processes for the production thereof, methods for controlling undesirable plant growth with the aid of the disclosed 2-nitrophenylhydrazines, and compositions containing said 2-nitrophenylhydrazines as the herbicidally active substances.

Also in the prior art is West German Offenlegungsschrift No. 2,349,228 (published Apr. 18, 1974). This reference is directed to substituted nitrophenylhydrazines as pre- and postemergent herbicides and plant growth regulators, including 1-(α, am α-trifluoro-2,6-dinitro-p-toluidino)piperidine. This compound is disclosed, but there is no test data showing its herbicidal properties

SUMMARY OF THE INVENTION

This invention relates to novel substituted (α, α, α-trifluoro-2,6-dinitro-p-tolyl)hydrazines which are active as herbicides, and to novel herbicidal compositions and methods employing a substituted (α, α, α-trifluoro-2,6-dinitro-p-tolyl)hydrazine as the herbicidally active ingredient.

DESCRIPTION OF THE PREFERRED EMBODIMENT

The novel compounds of this invention are of a class having the formula:

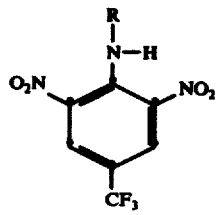

wherein
R is selected from the group consisting of 2,5-dimethylpyrrolidino, 2-ethylpiperidino, and 2,6-dimethylpiperidino.

These novel compounds possess activity as herbicides. The novel compounds of this invention have shown herbicidal activity in the greenhouse when applied at rates of from about 0.28 to about 8.96 kg./ha.

The novel compounds of this invention are readily prepared by methods well known to those skilled in the art. Thus, preparation of the novel compounds is carried out by allowing 4-chloro-3,5-dinitrobenzotrifluoride (commercially available) to react with a slight excess of a substituted hydrazine in a suitable solvent, such as ethanol, in the presence of a base, which can be an excess of the hydrazine, or an added base, such as triethylamine, at an elevated temperature for a time sufficient to bring about essentially complete reaction. The substituted hydrazines used in the preparation of the novel compounds of this invention include 1-amino-2,6-dimethylpiperidine, 1-amino- 2-ethylpiperidine, and 1-amino-2,5-dimethylpyrrolidine, all of which are commercialy available.

For example, the preparation is accomplished by suspending or dissolving 4-chloro-3,5-dinitrobenzotrifluoride, 1-amino-2-ethylpiperidine, and triethylamine in ethanol, and heating the reaction mixture to reflux temperature for a period of about 2 hours. The reaction product mixture is worked up by allowing it to cool and then refrigerating it for a time. The crystalline product which separates is filtered off and is identified by NMR spectrum and elemental analyses as, in the present example, 2-ethyl-1-(α, α, α-trifluoro-2,6-dinitro-p-toluidino)piperidine.

The following examples illustrate the preparation of novel compounds of the invention, but are not to be construed as limiting the scope of the invention.

EXAMPLE 1

2,6-Dimethyl-1-(α, α, α-trifluoro-2,6-dinitro-p-toluidino)-piperidine

A mixture of 5.5 g. (20 mmole) of 4-chloro-3,5-dinitrobenzotrifluoride and 5.4 g. (42 mmole) of 1-amino-2,6-dimethylpiperidine in 90 ml. of commercial ethyl alcohol was refluxed for about 2 hours. The excess of the piperidine compound (the substituted hydrazine) served as the base in this reaction. The reaction mixture was worked up by concentrating it in vacuo, leaving a residue. The residue was dissolved in benzene and chromatographed on a silica gel column using benzene as the eluant. The first band was collected and the solvent was removed in vacuo to leave a residue. The residue crystallized after cooling and scratching. The crystalline product had a melting point of about 53°-56° C., and weighed about 5.0 g. It was identified by NMR spectrum and elemental analyses as 2,6-dimethyl-1-(α, α, α-trifluoro-2,6-dinitro-p-toluidino)piperidine.

Analyses: Calculated for $C_{14}H_{17}F_3N_4O_4$: C, 46.41; H, 4.73; N, 15.46. Found: C, 46.14; H, 4.53; N, 15.21.

EXAMPLE 2

2-Ethyl-1-(α, α, α-trifluoro-2,6-dinitro-p-toluidino)piperidine

A mixture of 5.4 g. (20 mmole) of 4-chloro-3,5-dinitrobenzotrifluoride 2.7 g. (21 mmole) of 1-amino-2-ethylpiperidine, and 2.2 g. (21 mmole) of triethylamine in 100 ml. of commercial ethyl alcohol was refluxed for about 2 hours. The reaction product mixture was allowed to cool and to stand overnight. Some product crystallized out. The reaction product mixture was placed in the refrigerator for about 3 hours and was then filtered. The solid material which was obtained on the filter had a melting point of about 105°-107° C., and weighed about 6.8 g. It was identified by NMR spectrum and elemental analyses as 2-ethyl-1-(α, α, α-trifluoro-2,6-dinitro-p-toluidino)piperidine.

Analyses: Calculated for $C_{14}H_{17}F_3N_4O_4$: C, 46.41; H, 4.73 Found: C, 46.70; H, 4.58.

Following the same general procedure of Example 2, and using 4-chloro-3,5-dinitrobenzotrifluoride and 1-amino-2,5-dimethylpyrrolidine as starting materials, the following additional compound was prepared:

Mixture of cis and trans 2,5-dimethyl-1-(α, α, α-trifluro-2,6-dinitro-p-toluidino)pyrrolidine, having a melting point of about 66°-81° C. and weighing about 4.5 g.

It was identified by NMR spectrum and elemental analyses.

Analyses: Calculated for $C_{13}H_{15}F_3N_4O_4$: C, 44.83; H. 4.34; N, 16.09 Found: C, 45.00; H, 4.07; N, 16.06.

For use as preemergent selective herbicides, the compounds are formulated into compositions desirably containing, in addition to the substituted hydrazine, one or more of a plurality of additaments including water, polyhydroxy compounds, petroleum distillates, and other dispersion media, surface-active dispersing agents, emulsifiers, and finely-divided inert solids. The concentation of the substituted hydrazine compound in these compositions may vary depending on whether the composition is intended as an emulsifiable concentrate or a wetting powder designed to be subsequently diluted with additional inert carrier, such as water, to produce the ultimate treating composition, or is intended for direct application as a dust to plants.

Thus, treating compositions are most conveniently formulated by preparing liquid or solid concentrates, which are subsequently diluted to the desired level for use. Emulsifiable liquid concentrates can be prepared by incorporating from about 1 to about 30 percent by weight of the active ingredient and an emulsifying agent in a suitable water-immiscible organic liquid. Such concentrates may be further diluted with water to form spray mixtures in the form of oil-in-water emulsions. Such spray compositions then comprise active herbicide, water-immiscible solvent, emulsifying agent, and water. Suitable emulsifying agents can be of the non-ionic or ionic types, or blends thereof, and include condensation products of alkylene oxides with phenols and organic acids, polyoxyethylene derivatives of sorbitan esters, such as polyoxyethylene sorbitan mono-oleate, polyoxyethylene sorbitan mono-laurate; complex ether alcohols, such as polyglycol ether sulfonate; ionics of the aralkyl sulfonate type, such as alkylamine dodecylbenzene sulfonate, and the like. Suitable water immiscible organic liquids to be employed include aromatic hydrocarbons, aliphatic hydrocarbons, cycloaliphatic hydrocarbons and mixtures thereof, such as petroleum distillates.

Solid concentrate mixtures can be prepared by incorporating from about 1 to about 90 percent by weight of the substituted hydrazine compound in a finely divided inert solid carrier such as bentonite, fuller's earth, diatomaceous silica expanded mica, talc, chalk, and the like. Dispersing and/or wetting agents can be incorporated along with the substituted hydrazine in the solid carrier to form wettable powder concentrates ranging from 1 to 75 percent by weight concentration which subsequently can be dispersed in water or other hydroxylated carrier to form spray compositions. Suitable surfactants include condensed aryl sulfonic acids and sodium salts thereof, sodium lignosulfate, sulfonate oxide condensate blends, alkyl aryl polyether alcohols, sulfonated non-ionic blends, anionic wetting agents, and the like.

Spreadable granules can be prepared using calcined attapulgite clay as the solid diluent. Dry dispersions can be prepared on herbicidally inert carriers, such as vermiculite, peat moss, and the like.

The novel compounds of this invention can be used for treating a soil area or locus infested with weed grass seeds with a dust, granular formulation, or spray containing one or more of the novel compounds as the herbicidally active ingredient. Typical of soil areas which can be treated are crop growing areas in which tolerant crops are being grown; and in miscellaneous places, such as gravel driveways, clay tennis courts, walks, road shoulders, and the like where the elimination of grasses is desired. As is well understood in the art, the application rates required when the compounds are to be used in the field are greater than those mentioned above as being required in the greenhouse. In the use of the invention on a practical basis, compositions containing the herbicidally-active compound can be sprayed, dusted, or spread by methods well known to the art onto the particular area at the rate of around 1.12 kg./ha. to 36 kg./ha., or somewhat more if necessary, for example, 56 kg. of active ingredient per hectare.

As pointed out above, the novel compounds of this invention are active as herbicides, mainly as preemergent herbicides. The herbicidal activity has been established by tests which have been carried out as described hereinafter Experiment 1

A soil was prepared consisting of one part masonry sand and one part shredded top soil blended together. Plantings were made in galvanized metal flats which measured 31.5 cm. long, 21.5 cm. wide, and 8 cm. deep, with holes and grooves in the bottom for drainage. Each flat was filled two-thirds full with soil and the soil was leveled and tamped. All the seeds were planted in rows perpendicular to the long axis of the flat, one species per row. The large seeds of morningglory and corn were planted in rows about 1 cm. deep made by a hand-held press. The remainder of the seeds, that is, the small seeds, were planted by sprinkling the seeds in rows on the surface of the prepared soil in the trays, and then all of the seeds were covered with from 0.5 cm. to 1.0 cm. of sifted soil. The approximate number of seeds planted per species are as follows:

Corn (*Zea mays*) 4
Morningglory (*Ipomoea purpurea*) 25
Zinnia (*Zinnia elegans*) 20
Foxtail millet (*Setaria italia*) 200
Large crabgrasss (*Digitaria sanguinalis;* ) 350
Velvetleaf (*Abutilon theophrasti*) 100
Pigweed (*Amaranthus retroflexus*) 350

Two and one-half g. of soluble fertilizer was applied to each flat during the first watering after planting. The postemergence flats were planted 10–13 days prior to treatment and were then placed in a growth chamber until the day of treatment. The flats were given 12–18 hours of light each day, depending on light intensity, and subjected to a temperature of 74°–80° F. The preemergence flats were planted the same day the treatments were applied. After treatment, all the flats were moved into a greenhouse.

The compounds studied in this test were applied at the rate ot 8.986 kg./ha. The formulation for an application rate of 8.96 kg./ha. was accomplished by dissolving 120 mg. of the test compound in about 2.5 ml. of a solvent containing acetone and ethyl alcohol in a 1:1 ratio together with a small amount of Toximul R and S. The solution was then diluted with deionized water to a volume of about 25 ml. Toximul R and Toximul S are sulfonate/non-ionic blends which are products of Stepan Chemical Company, Northfield, Ill.

The herbicidal compositions were applied to each flat with a modified DeVilbiss atomizer hooked to an air source. In the preemergent test, the herbicidal compositions were sprayed on the surface of the soil in the flat after the seeds were planted. In the postemergent test, the herbicidal compositions were sprayed on the foliage of the plants 10–13 days after planting the seeds from which the plants grew. Twelve and one-half ml. of the composition under test was applied to each flat. This is equal to an 8.96 kg./ha. application rate.

After treatment, all the flats were transferred to the greenhouse for 12–13 days. Herbicidal effects were then rated on each plant species. The ratings were based on a 1 to 5 scale:
 1 = no injury
 2 = slight
 3 = moderate
 4 = severe
 5 = death Table 1, which follows, sets forth the results of the testing of the compounds. In the table, column 1 identifies the compound by its operating example number in the specification; column 2, the rate in terms of kg./ha. at which the compound was applied to the test flat; columns 3 t 9, the injury rating for particular plant seedlings.

The test plants are identified by letters of the alphabet, as set forth hereinbelow:
 A — Corn
 B — Large crabgrass
 C — Pigweed
 D — Foxtail
 E — Velvetleaf
 F — Morningglory
 G — Zinnia

TABLE 1

| Comp. | Appln. Rate kg./ha. | Plant Injury Ratings Pre-emergence A B C D E F G | Post-emergence A B C D E F G |
|---|---|---|---|
| 1 | 8.96 | 3 4 4 5 3 2 2 | 1 3 3 3 3 2 3 |
| 2 | 8.96 | 1 4 2 3 2 1 1 | 1 1 1 1 1 1 1 |
| 3 | 8.96 | 1 4 3 4 3 1 1 | 3 3 2 3 3 2 3 |

EXPERIMENT 2

Further testing of certain of the compounds falling within the scope of the above generic formula as preemergent herbicides was carried out against a broader spectrum of plants. The plant species used in this experiment were planted in galvanized pans exactly like those used in Experiment 1, using the same type of soil. Each flat was filled two-thirds with the prepared soil and the soil leveled and tamped. In these preemergence tests, two flats containing 10 indicator species each were used for each application rate of each chemical. The seeds of the species of plants were planted in rows parallel to the long axis of the flat, one species per half row, in the same manner as in Experiment 1. The approximate numbers of seeds planted are as follows:
 A — Corn (*Zea mays*) 4
 B — Cotton (*Gossypium hirsutum*) 6
 C — Soybean (*Glycine max*) 6
 D — Wheat (*Triticum aesitivum*) 40
 E — Alfalfa (*Medicago sativa*) 100
 F — Sugarbeet (*Beta vulgaris*) 25
 G — Rice (*Oryza sativa*) 46
 H — Cucumber (*Cucumis sativus*) 8
 J — Tomato (*Lycoperisicon esculentum*) 30
 K — Barnyard grass (*Echinochloa crus-galli*) 50
 L — Lambsquarter (*Chenopodium album*) 100
 M — Large crabgrass (*Digitaris sanguinalis*) 100
 N — Mustard (*Brassica juncea*) 50
 O — Pigweed (*Amaranthus retroflexus*) 150
 P — Foxtal millet (*Setaria italia*) 100
 Q — Wild oat (*Avena fatua*) 25
 R — Velvetleaf (*Abutilon theophrasti*) 25
 S — Morningglory (*Ipomoea purpurea*) 15
 T — Zinnia (*Zinnia elegans*) 20

For this preemergence testing, the flats were planted the same day as the treatments were applied, and the seeds were covered with 0.5 to 1.0 cm. of soil. The chemicals were formulated the same way as described in Experiment 1 and then serialy diluted to provide the desired concentrations of test solutions for applications at the desired rate. Chemicals were applied to the surface of the flats using a modified DeVilbiss atomizer connected to an air source. Each flat received 12.5 ml. of spray solution. The flats were maintained in the greenhouse after the treatment.

The herbicidal effects of the chemicals were evaluated about 18–21 days after preemergence applications. The degree of plant injury is based on a 1 to 5 scale and a single numerical rating was assigned to each plant species as follows:
 1 = no injury
 2 = slight injury
 3 = moderate injury
 4 = severe injury
 5 = death Table 2, which follows, sets forth the results of the preemergent testing of the compounds against crops, grasses, and broadleaf weeds. In the table, column 1 identifies the compound; column 2, the rate in terms of kg./ha. at which the compound was applied to the test flat; and the remainder of the columns, the injury rating for the particular plant seedlings. Where more than one replicate was run, the injury rating is an average value.

TABLE 2

| Compound | Appln. Rate kg./ha. | A | B | C | D | E | F | G | H | J | K | L | M | N | O | P | Q | R | S | T |
|---|---|---|---|---|---|---|---|---|---|---|---|---|---|---|---|---|---|---|---|---|
| 1 | 0.28 | 1 | 1 | 1 | 1 | 1 | 2 | 1 | 1 | 2 | 3 | 2 | 3 | 1 | 2 | 2 | 1 | 2 | 1 | 1 |
|  | 0.56 | 1 | 1 | 1 | 1 | 1 | 2 | 1 | 2 | 2 | 3 | 3 | 4 | 1 | 3 | 4 | 1 | 3 | 1 | 2 |
|  | 1.12 | 1 | 1 | 1 | 1 | 1 | 2 | 1.5 | 2 | 2.5 | 2 | 3 | 4 | 2.5 | 2.5 | 4 | 2 | 2.5 | 1.5 | 1.5 |
|  | 2.24 | 3 | 1 | 2 | 1 | 1 | 3 | 2 | 2 | 3 | — | 3 | 5 | 2 | 2 | 4 | 3 | 2 | 2 | 2 |
|  | 4.48 | 4 | 1 | 1 | 1 | 2 | 3 | 2 | 3 | 3 | — | 3 | 5 | 3 | 3 | 4 | 3 | 2 | 3 | 2 |
| 3 | 1.12 | 1 | 1 | 1 | 1 | 1 | 1 | 1 | 1 | 1 | 4 | 2 | 2 | 1 | 2 | 2 | 1 | 1 | 1 | 1 |
|  | 2.24 | 1 | 1 | 1 | 1 | 1 | 1 | 1 | 1 | 2 | 4 | 2 | 4 | 1 | 3 | 4 | 2 | 2 | 1 | 1 |
|  | 4.48 | 1 | 1 | 1 | 2 | 1 | 1 | 1 | 1 | 2 | 4 | 3 | 4 | 2 | 3 | 4 | 2 | 3 | 2 | 1 |

EXPERIMENT 3

One of the novel compounds was selected to be run in a test to determine its herbicidal efficacy and the tolerance of crops when the compound was pre-plant soil-incorporated. The tests were carried out in a level field containing silt loan having an organic content of about 2 percent (estimated). The soil contained small clods and was dry at a depth of 1 cm. Soil moisture was regarded as being intermediate and the only water source was rainfall. The randomized block experimental design was used. Three replicates of each treatment were run. The field was divided into slots each measuring 17 × 4 feet. Sixteen rows, each 9 inches wide, were prepared in each slot, the remaining space being accounted for by tractor-wheel tracks, and an area 1 × 4 feet at the end of each plot. The test compound, identified as compound 1 (from Example 1), was formulated as a 25 percent by weight emulsifiable concentrate. This formulation was then diluted with water to provide the application rates desired for this test. The test compound was applied by a $CO_2$ constant rate sprayer in a band 3 feet wide and 17 feet long through the center of each plot, and was then immediately incorporated into the soil. The crops were then planted.

The crops and varieties used are listed hereinbelow:
corn, M5040
soybean, Wayne
snapbean, Tender Green Imp
cotton, Stoneville 213
cantaloupe, Delicious 51
peanut, Florigiant
rice, Nato
sorghum, RS610
rape, Zephyr
wheat, Arthur
tomato, Heinz 1350
alfalfa, Vernal
sugarbeet, Monogerm
cabbage, Marion Market
wild oat, *Avena fatua*
red root pigweed, *Amaranthus retroflexus*
foxtail millet, *Setaria italica*

These crops were planted in rows perpendicular to the plot length. The rows were 9 inches wide.

The plants were observed at 26 and at 47 days after treatment (DAT). The observations made were for determining the percent weed control, the percent injury to grass crops, and the percent injury to broadleaf crops. The results are set forth in the tables which follow. In Table 3, which follows, column 1 identifies the test compounds; column 2 lists the application rate in kh./ha.; and the percent weed control on the designated DAT for the particular weed is listed in the remaining columns.

TABLE 3

| Compound No. | Rate kg./ha. | Percent Weed Control | | | | | |
|---|---|---|---|---|---|---|---|
| | | Pigweed | | Foxtail | | Wild Oat | |
| | | 26 | 47 | 26 | 47 | 26 | 47 |
| 1 | 0.56 | 50 | 42 | 37 | 40 | 13 | 50 |
| | 1.12 | 98 | 73 | 85 | 73 | 27 | 30 |
| | 2.24 | 99 | 91 | 96 | 87 | 40 | 57 |
| | 4.48 | 100 | 98 | 99 | 97 | 43 | 47 |

Table 4, which follows, reports the percent injury to grass crops. In the table, column 1 identifies the test compound; column 2 identifies the application rate in kg./ha.; and the remainder of the columns list the percent injury to the particular grass crop at the indicated DAT.

TABLE 4

| Cmp. No. | Rate kg./ha. | Percent Injury to Grass Crops | | | | | | | |
|---|---|---|---|---|---|---|---|---|---|
| | | Corn | | Sorghum | | Wheat | | Rice | |
| | | 26 | 47 | 26 | 47 | 26 | 47 | 26 | 47 |
| 1 | 0.56 | 13 | 50 | 7 | 20 | 13 | 20 | 27 | 10 |
| | 1.12 | 31 | 42 | 43 | 27 | 23 | 7 | 37 | 37 |
| | 2.24 | 41 | 57 | 47 | 50 | 43 | 17 | 57 | 47 |
| | 4.48 | 62 | 73 | 99 | 93 | 60 | 60 | 73 | 77 |

Table 5, which follows, reports the percent injury to broadleaf crops. In the table, column 1 identifies the test compound; column 2 gives the application rate in kg./ha.; and the remainder of the columns in the table list the percent injury to the identified broadleaf crop at the indicated DAT.

TABLE 5

| Cmp. No. | Rate kg./ha. | Percent Injury to Broadleaf Crops | | | | | | | | | | | | | | | | | |
|---|---|---|---|---|---|---|---|---|---|---|---|---|---|---|---|---|---|---|---|
| | | Soybean | | Snapbean | | Cotton | | Rape | | Tomato | | Alfalfa | | Sugar Beet | | Cabbage | | Peanuts | | Cantaloupe | |
| | | 26 | 47 | 26 | 47 | 26 | 47 | 26 | 47 | 26 | 47 | 26 | 47 | 26 | 47 | 26 | 47 | 26 | 47 | 26 | 47 |
| 1 | 0.56 | 13 | 0 | 17 | 50 | 17 | 0 | 0 | 0 | 33 | 50 | 10 | 50 | 13 | 50 | 13 | 50 | 27 | 10 | 20 | 30 |
| | 1.12 | 7 | 3 | 27 | 57 | 10 | 37 | 10 | 15 | 50 | 33 | 43 | 57 | 70 | 67 | 60 | 70 | 20 | 13 | 27 | 20 |
| | 2.24 | 10 | 7 | 30 | 53 | 10 | 10 | 20 | 10 | 100 | 100 | 47 | 50 | 97 | 90 | 73 | 97 | 30 | 33 | 30 | 7 |
| | 4.48 | 37 | 27 | 23 | 47 | 33 | 23 | 70 | 80 | 100 | 100 | 87 | 90 | 80 | 77 | 60 | 77 | 50 | 33 | 57 | 20 |

EXPERIMENT 4

This experiment was run to determine the herbicidal efficacy and crop tolerance of Compound 1 when the compound was applied as a preemergence surface spray application. In this experiment, the same crop and weed seeds as were used in Experiment 3, were planted in plots the same size as those used in Experiment 3, and the same number of replicates of treatments were run as in Experiment 33. The same type of soil texture, organic content and the like were present in this experiment also. The seeds were planted in the same manner and the test compound, Compound 1, formulated as a 25 percent by weight emulsifiable concentrate was diluted with water to provide the application rate compositions desired. The compositions were applied to the surface of the soil using a $CO_2$ constant rate sprayer after the seeds were planted.

The percent weed control, percent injury to grass crops and percent injury to broadleaf crops were determined by observations conducted 16 and 44 days after treatment (DAT). The results are reported in the tables which follow.

The percent weed control is reported in Table 6 which follows. In the table, column 1 identifies the test compound; column 2, the application rate in kg./ha.; and the remainder of the columns in the table list the percent weed control observed at the indicated DAT.

TABLE 6

| Cmp. No. | Rate kg./ha. | Percent Weed Control | | | | | |
|---|---|---|---|---|---|---|---|
| | | Pigweed | | Foxtail | | Wild Oat | |
| | | 16 | 44 | 16 | 44 | 16 | 44 |
| 1 | 1.12 | 50 | 47 | 73 | 50 | 33 | 20 |
| | 2.24 | 53 | 52 | 77 | 65 | 20 | 30 |
| | 4.48 | 95 | 93 | 96 | 90 | 57 | 17 |

Table 7, which follows, reports the percent injury to grass crops. In the table, column 1 identifies the test compound; column 2, the application rate in kg./ha.; and the remainder of the columns list the percent injury to the individual grass crop observed at the indicated DAT.

TABLE 7

| Cmp. No. | Rate kg./ha. | Percent Injury to Grass Crops | | | | | | | |
|---|---|---|---|---|---|---|---|---|---|
| | | Corn | | Sorghum | | Wheat | | Rice | |
| | | 16 | 44 | 16 | 44 | 16 | 44 | 16 | 44 |
| 1 | 1.12 | 18 | 25 | 20 | 30 | 20 | 0 | 30 | 60 |
| | 2.24 | 7 | 0 | 3 | 0 | 7 | 0 | 13 | 0 |
| | 4.48 | 10 | 0 | 7 | 3 | 20 | 0 | 40 | 23 |

In Table 8, there is reported the percent injury to broadleaf crops. In the table, which follows, column 1 identifies the test compound; column 2 the application rate in kg./ha.; the remainder of the columns list the percent injury to the particular broadleaf crop observed at the indicated DAT.

TABLE 8

| Cmp. No. | Rate kg./ha. | Percent Injury to Broadleaf Plants | | | | | | | | | | | | | | | | | | |
|---|---|---|---|---|---|---|---|---|---|---|---|---|---|---|---|---|---|---|---|---|
| | | Soybean | | Snapbean | | Cotton | | Rape | | Tomato | | Alfalfa | | Sugar Beet | | Cabbage | | Peanuts | | Cantaloupe | |
| | | 16 | 44 | 16 | 44 | 16 | 44 | 16 | 44 | 16 | 44 | 16 | 44 | 16 | 44 | 16 | 44 | 16 | 44 | 16 | 44 |
| 1 | 1.12 | 23 | 0 | 3 | 0 | 10 | 0 | 30 | 0 | 13 | 70 | 20 | 30 | 43 | 20 | 43 | 0 | 13 | 40 | 27 | 0 |
| | 2.24 | 3 | 0 | 10 | 0 | 0 | 0 | 50 | 0 | 50 | 80 | 33 | 0 | 30 | 20 | 43 | 20 | 17 | 30 | 27 | 20 |
| | 4.48 | 17 | 0 | 13 | 7 | 37 | 7 | 93 | 97 | 87 | 87 | 87 | 77 | 73 | 83 | 77 | 87 | 20 | 17 | 60 | 33 |

The results appearing in the tables show that the compounds are most active as preemergent herbicides.

I claim:

1. A compound of the formula

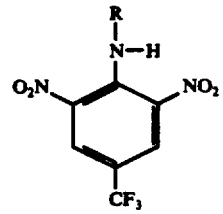

wherein
R is selected from the group consisting of 2,5-dimethylpyrrolidino and 2,6-dimethylpiperidino.

2. A compound as in claim 1, said compound being 2,6-dimethyl-1-($\alpha$, $\alpha$, $\alpha$-trifluoro-2,6-dinitro-p-toluidino) piperidine.

3. A compound as in claim 1, said compound being 2,5-dimethyl-1-($\alpha$, $\alpha$, $\alpha$-trifluoro-2,6-dinitro-p-toluidino)pyrrolidine.

4. A method of controlling unwanted vegetation which comprises the preemergent application to the locus of the vegetation a herbicidally-effective amount of a compound of claim 1.

5. The method of claim 4 wherein the herbicidal compound is applied at the rate of from about 1.12 to about 56 kg./ha.

6. The method of claim 4 wherein the herbicidal compound is applied at the rate of from about 1.12 to about 8.96 kg./ha.

7. The method of claim 4 wherein the herbicidal compound is 2,6-dimethyl-1-($\alpha$, $\alpha$, $\alpha$-trifluoro-2,6-dinitro-p-toluidino)piperidine.

* * * * *